United States Patent [19]

Grenner et al.

[11] Patent Number: 5,395,995
[45] Date of Patent: Mar. 7, 1995

[54] PROCESS FOR THE PREPARATION AND PURIFICATION OF NITROAROMATICS

[75] Inventors: Dieter Grenner, Leverkusen; Thomas Schieb, Roesrath; Gerhard Wiechers, Leverkusen, all of Germany

[73] Assignee: Bayer Aktiengesellschaft, Leverkusen, Germany

[21] Appl. No.: 59,783

[22] Filed: May 10, 1993

[30] Foreign Application Priority Data

May 18, 1992 [DE] Germany .............. 42 16 416.8

[51] Int. Cl.$^6$ .............. C07C 201/08; C07C 201/16; C07C 205/06
[52] U.S. Cl. .............. 568/934; 568/932; 568/935; 568/939; 568/940
[58] Field of Search .............. 568/934, 935, 940, 932, 568/939

[56] References Cited

U.S. PATENT DOCUMENTS

| | | | |
|---|---|---|---|
| 2,815,364 | 12/1957 | Green | 568/940 |
| 2,886,587 | 5/1959 | Kolmer | 568/940 |
| 4,026,955 | 5/1977 | Breaux et al. | 568/938 |
| 4,147,732 | 4/1979 | Mendiratta | 568/938 |
| 4,642,396 | 2/1987 | Carr et al. | 568/934 |
| 4,918,250 | 4/1990 | Mason et al. | 568/934 |
| 5,001,272 | 3/1991 | Mason | 568/934 |
| 5,057,632 | 10/1991 | Imm et al. | 568/934 |

FOREIGN PATENT DOCUMENTS

| | | |
|---|---|---|
| 022241 | 1/1981 | European Pat. Off. . |
| 169441 | 1/1986 | European Pat. Off. . |
| 8912620 | 12/1989 | WIPO . |

*Primary Examiner*—Joseph E. Evans
*Attorney, Agent, or Firm*—Joseph C. Gil; Lyndanne M. Whalen

[57] ABSTRACT

A process for the preparation and purification of nitroaromatics by nitration of the corresponding aromatics and subsequent melt crystallization. The residual melts which occur are recycled.

5 Claims, No Drawings

PROCESS FOR THE PREPARATION AND PURIFICATION OF NITROAROMATICS

BACKGROUND OF THE INVENTION

The present invention relates to a process for the preparation and purification of nitroaromatics.

Nitroaromatics constitute valuable intermediates for dye synthesis, primary products for plastics (e.g., toluylenediisocyanate and diphenylmethanediisocyanate), plant protection products, etc. Such nitroaromatic compounds are generally reduced to the corresponding amines, which are then further processed.

Nitroaromatics are prepared industrially by reacting aromatic hydrocarbons with nitric acid in the liquid phase in the presence of a Lewis acid catalyst. Commodity chemicals, especially, nitrobenzenes and nitrotoluenes having one or more nitro groups, are obtained in this manner. Mixtures of sulfuric acid and nitric acid of varying concentrations are used for the reaction. The literature also describes processes which work with only nitric acid (U.S. Pat. No. 4,918,250; U.S. Pat. No. 5,001,272 and WO 89/12620) or $N_2O_4/O_2$ mixtures (EP 169 441 and EP 173 131) in the liquid phase.

Common features of the known processes for producing nitroaromatics are: 1) the nitroaromatics are separated from the aqueous acid and the water produced by the reaction, and 2) neutralization of the acids dissolved in the nitroaromatic is performed with basic substances (e.g. with metal oxides, metal hydroxides, metal carbonates, metal hydrogen carbonates, ammonia, amines, etc.). These bases are used in the form of aqueous solutions in order to wash the nitroaromatic free of acid. The nitroaromatic is further scrubbed with fully deionized water in order to remove dissolved salts from the nitroaromatic. A considerable effluent volume (approx. 50 to 1000 kg effluent per tonne of nitroaromatic) results. This effluent is heavily contaminated with inorganic salts such as nitrates, sulfates and nitrated aromatic compounds (nitroaromatics, nitrophenol derivatives, nitrobenzoic acids, etc.).

Nitrated aromatic compounds are known to be difficult to degrade in biological treatment plants. Inorganic nitrates are partly responsible for the increased nitrogen input to the natural environment. Effluents from the production of nitroaromatics must therefore be extensively treated in order to remove these pollutants before leading to a waste water treatment plant.

Another possible route for separation of the aqueous acid from the nitration mixture is the crystallization of the nitroaromatics out of the solution. For example, U.S. Pat. No. 5,057,632 describes the possibility of separating dinitrotoluene from the reaction solution by single-stage crystallization. However, this separation technique changes the isomer ratio in the dinitrotoluene. Further purification of the crystallized dinitrotoluene to separate from normally present inorganic and organic acids is not described.

DE 2 926 947 discloses that nitrosation agents can be removed from the nitroaromatics after nitration of the nitroaromatics by crystallization. However, it is then necessary to separate and wash the compound which crystallizes out with a pH-neutral material, in order to remove other organic and inorganic acids from the product.

SUMMARY OF THE INVENTION

It is therefore an object of the present invention to provide a process which enables pure nitroaromatic compounds to be produced without the simultaneous requirement for technically elaborate and costly purification steps and without the occurrence of large volumes of waste water.

This and other objectives which will be apparent to those skilled in the art are accomplished by nitrating an aromatic compound and melt crystallizing the nitroaromatic compound containing mixture.

DETAILED DESCRIPTION OF THE PRESENT INVENTION

The present invention provides a process for the preparation of pure nitroaromatic compounds (including isomer mixtures such as those which are typically formed in nitration reactions) by the nitration of the corresponding aromatic compound(s) with aqueous nitric acid or nitrating acid at temperatures above that at which the organic phase is solid. An emulsion of aqueous liquid phase in organic liquid phase, an emulsion of organic liquid phase in an aqueous liquid phase, or a solution forms. The aqueous phase is separated from the organic phase if two such phases are formed. If a solution is formed, the solution may be converted into two phases by means of auxiliary substances. The two phases may then be separated to remove the nitric acid from solution. The nitric acid may also be removed from the solution by distillation. The organic phase (i.e., the nitroaromatic compound containing mixture) is subjected to one or more melt crystallization steps. The residual melt(s) remaining after the crystallization(s) is (are) separated and returned into the nitration vessel and/or into the reaction sequence upstream of the phase separation.

All inorganic and organic acids are removed from the nitroaromatic compounds by the process of the present invention without the need for an aqueous neutral or alkaline wash or neutralization of the nitroaromatic compounds. No inorganically or organically contaminated wash waters are produced as a result.

Suspension crystallization or layer crystallization may be performed as a suitable melt crystallization. After separation of what is termed the "residual melt", the crystals are freed of any normally occurring contaminants by what is termed "sweating", i.e. partial melting down and separation of the liquid phase. The residual melts are returned to the nitration vessel and/or into the reaction sequence upstream of the phase separation.

The liquid product is cooled down very slowly which results in formation of a three dimensional network of crystals. When a major part of the melt has crystallized, the remaining liquid phase (residual melt) is separated. Then the crystalline product is heated up carefully which causes partial melting (sweating) of the crystals. The liquid phase is separated and combined with the previous residual melt. This process may be repeated several times.

The acidic components are returned to the nitration vessel and/or fed to the acid preparation in the process of the present invention. The isomer distribution of the product after melt crystallization corresponds to the isomer distribution which occurs in nitration.

The following compounds are examples of aromatic compounds which may be nitrated in accordance with the process of the present invention:

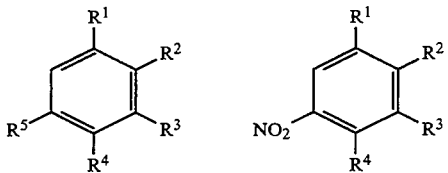

in which

R[1], R[2], R[3], R[4], and R[5] may represent independently of one another, hydrogen, an alkyl group, aryl group, F, Cl, Br, I, $NO_2$, an O-alkyl group, O-aryl group or an OH group.

Benzene, nitrobenzene, toluene, nitrotoluene, chlorobenzene, dilchlorobenzene, chlorotoluene, dinitrotoluene and isomer mixtures thereof are preferably nitrated in accordance with the process of the present invention.

The invention is explained in greater detail with the aid of the Examples below.

EXAMPLE 1

450.0 g (7.0 mole) of 98% nitric acid were added dropwise to 92.1 g (1.0 mole) toluene in a manner such that a temperature of 70° C. was not exceeded (reaction and post-addition stirring phase approx. 1 h). Acid and water produced by the reaction were then distilled off under vacuum as much as possible. The nitrated product remaining in the sump was diluted with residual melt from previous experiments and cooled to room temperature. The crystallized portion was separated from the liquid portion by suction filtration. The crystallized product contained no further acid. No aqueous post-treatment was necessary. The 2,4-dinitrotoluene to 2,6-dinitrotoluene isomer ratio of the dinitrotoluene prepared was 8:2. The liquid portion of the nitro product (residual melt) was added to the next crystallization charge.

EXAMPLE 2

584.8 g crude dinitrotoluene from a reaction of toluene with nitrating acid was cooled from approx. 65° C. to 37° C. at a rate of approximately 0.3° C./min. The crystalline portion was then separated from the residual melt by suction. The crystals contained no acid or other undesirable contaminants, thus obviating the need for additional purification, e.g., by washing.

EXAMPLE 3

447.4 g of a mixture of crude dinitrotoluene (DNT) having the following composition: 3,35 wt % of 2,3 DNT, 56,57 wt % of 2,4 DNT, 1,05 wt % of 2,5-DNT, 34,88 wt % of 2,6-DNT, 4,14 wt % of 3,4-DNT obtained from residual melt from a previous run and crude dinitrotoluene (composition: 2,3-DNT 1,38 wt %, 2,4-DNT 76,42 wt %, 2,5-DNT 0,57 wt %, 2,6-DNT 19,16 wt %, 3,4-DNT 2,47 wt %) were cooled from approximately 65° C. to 28° C. at a rate of 0.2° C./min. The isomer composition of the crystals drawn off by suction was as follows: 2,03 wt % of 2,3-DNT, 76,25 wt % of 2,4-DNT, 0,57 wt % of 2,5-DNT, 19,06 wt % of 2,6-DNT and 2,10 wt % of 3,4-DNT. The isomer ratio of 2,4-DNT to 2,6-DNT was 8:2. The crystals no longer contained undesirable contaminants or acid, thus obviating the need for additional washing.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a nitroaromatic compound which is an isomer mixture of improved purity comprising:
    a) nitrating an isomer mixture of a nitroaromatic compound to form an emulsion or solution containing the corresponding nitroaromatic compound isomer mixture,
    b) separating any aqueous phase from the organic phase containing the nitroaromatic compound isomer mixture,
    c) melt crystallizing the phase containing the nitroaromatic compound isomer mixture,
    d) recovering the nitroaromatic compound isomers in crystal form, and
    e) recycling the residue from d) to a vessel in which step a) is to be conducted or to the organic phase containing the nitroaromatic compound isomer mixture remaining after separation b).

2. A process for the production of a nitroaromatic compound of improved purity comprising:
    a) nitrating an aromatic compound with an aqueous solution of nitric acid to form a solution containing the corresponding nitroaromatic compound,
    b) adding an auxiliary agent to convert the solution to two phases,
    c) separating the aqueous phase from the organic phase containing the nitroaromatic compound,
    d) melt crystallizing the nitroaromatic compound containing phase,
    e) recovering the nitroaromatic compound in crystal form, and
    f) recycling the residue from e) to a vessel in which step a) is to be conducted or the organic phase containing the nitroaromatic compound remaining after separation c).

3. A process for the production of a nitroaromatic compound of improved purity comprising:
    a) nitrating an aromatic compound with an aqueous solution of nitric acid to form a solution containing the corresponding nitroaromatic compound,
    b) removing the nitric acid from the nitrated mixture by distillation,
    c) separating any aqueous phase from the organic phase containing the nitroaromatic compound,
    d) melt crystallizing the nitroaromatic compound containing phase,
    e) recovering the nitroaromatic compound in crystal form, and
    f) recycling the residue from e) to a vessel in which step a) is to be conducted or to the organic phase containing the nitroaromatic compound remaining after separation c).

4. A process for the production of a nitrotoluene compound of improved purity comprising:
    a) nitrating toluene to form an emulsion or solution containing nitrotoluene,
    b) separating any aqueous phase from the organic phase containing nitrotoluene, c) melt crystallizing the nitrotoluene containing phase, d) recovering the nitrotoluene in crystal form, and e) recycling the residue from d) to a vessel in which step a) is to be conducted or to the organic phase containing nitrotoluene remaining after separation b).

5. A process for the production of a dinitrotoluene of improved purity comprising:

a) nitrating a mononitrotoluene to form an emulsion or solution containing dinitrotoluene, b) separating any aqueous phase from the organic phase containing dinitrotoluene, c) melt crystallizing the dinitrotoluene containing phase, d) recovering the dinitrotoluene in crystal form, and e) recycling the residue from d) to a vessel in which step a) is to be conducted or to the organic phase containing dinitrotoluene remaining after separation b).

* * * * *